US005993822A

United States Patent [19]

Ritchie et al.

[11] Patent Number: 5,993,822

[45] Date of Patent: Nov. 30, 1999

[54] MODIFIED LIVE AVIAN POLYMAVIRUS VACCINE IN PSITTACINE BIRDS

[75] Inventors: Branson W. Ritchie, Athens; Phil D. Lukert, Colbert; Denise Pesti, Athens, all of Ga.

[73] Assignee: University of Georgia Research Foundation, Inc., Athens, Ga.

[21] Appl. No.: 08/868,903

[22] Filed: Jun. 4, 1997

Related U.S. Application Data

[60] Provisional application No. 60/019,236, Jun. 4, 1996.

[51] Int. Cl.[6] .......................... A61K 35/76; A61K 39/12

[52] U.S. Cl. .................... 424/204.1; 424/93.6; 424/816; 435/235.1; 435/236; 435/237; 435/239

[58] Field of Search ............................... 424/204.1, 93.6, 424/816; 435/235.1, 236, 237, 239

[56] References Cited

U.S. PATENT DOCUMENTS

| | | | |
|---|---|---|---|
| 5,523,088 | 6/1996 | Ritchie et al. | 424/204.1 |
| 5,747,045 | 5/1998 | Ritchie et al. | 424/204.1 |

OTHER PUBLICATIONS

Ritchie et al., "Polyomavirus Infections in Adult Psittacine Birds" *J. Assoc. Avian Vet.* 5:202–206 (1991).

Graham and Calnek, "Papovavirus Infection in Hand–Fed Parrots: Virus Isolation and Pathology" *Avian Diseases*31:398–410 (1985).

Ritchie et al., "Avian Polyomavirus: An Overview" *J. Assoc. Avian Vet.*5:12–14 (1991).

Stoll et al., "Molecular and biological characteristics of avian polyomaviruses: isolates from different species of birds indicate that avian polyomaviruses form a distinct subgenus within the polyomavirus genus" *J. Gen. Virology*74:229–237 (1993).

Gaskin, J. M., "Adverse Reactions to Currnet Pet Bird Vaccine" *J. Assoc. Avian Vet.*5:12–14 (1991).

Ritchie et al., "Efficacy of an Inactivated Avian Polyomavirus Vaccine" *J. Assoc. Avian Vet.*7:187–192 (1993).

Niagro et al., "Avian Polyomavirus: Discordance Between Neutralizing Antibody Titers and Viral Shedding in an Aviary" *Proceedings Association of Avian Veterinarians* 22–26 (1991).

Epstein et al., "Not all potentially neutralizing vaccine–induced antibodies to Epstein–Barr virus ensure protection of susceptible experimental animals" *Clin. Exp. Immunol.* 63:485–490 (1986).

Della–Porta et al., "An Experimental Inactivated Virus Vaccine Against Bovine Ephemeral Fever. 2. Do Neutralizing Antibodies Protect Against Infection?" *Veterinary Microbiology*4:197–208 (1979).

Dykstra et al., "Investigations of budgerigar fledgling disease virus" *Am. J. Vet. Res.* 45(9):1883–1887 (1984).

Ritchie et al., "Susceptibility of Avian Polyomavirus to Inactivation" *Journal of the Association of Avian Veternarians*7(4):193–195, 1993.

Ritchie et al., "Antibody Response and Local Reactions to Adjuvanted Avian Polyomavirus Vaccines in Psittacine Birds",*Journal of the Association of Avian Veterinarians* vol. 8, No. 1 pp. 21–26 (1994).

Lehn and Mueller, "Cloning and Characterization of Budgerigar Fledgling Disease Virus, an Avian Polyomavirus", *Virology,* 151, 362–370 (1986).

Wainwright, et al., "Serological Evaluation of Some Psittachformes for Budgerigar Fledgling Disease Virus", *Avian Diseases,*31:673–676, 1987.

Stoll et al. 1994 Journal of General Virology 75 (9) 2261–2269, Sep. 1994.

*Primary Examiner*—Chris Eisenschenk
*Assistant Examiner*—Mary K. Zeman
*Attorney, Agent, or Firm*—Needle & Rosenberg, P.C.

[57] ABSTRACT

The present invention provides a vaccine which is protective against avian polyomavirus infection in a bird which is classified as being a member of the Psittaciformes order which comprises an immunogenic amount of a modified live avian polyomavirus in a pharmaceutically acceptable carrier. Methods are also provided for preventing avian polyomavirus infection in a bird, or in several different species of birds, classified as being a member of the Psittaciformes order, comprising administering a vaccine comprising an immunogenic amount of a modified live avian polyomavirus and a pharmaceutically acceptable carrier. A preferred embodiment provides a modified live avian polyomavirus vaccine for prevention of wild-type infection in a Budgerigar, lovebird or Cockatiel.

12 Claims, No Drawings

MODIFIED LIVE AVIAN POLYMAVIRUS VACCINE IN PSITTACINE BIRDS

This application claims priority in Provisional Application Serial No. 60,019,236, filed Jun. 4, 1996.

BACKGROUND OF THE INVENTION

1. Field of the Invention

The present invention relates to an avian polyomavirus vaccine and to a method of preventing avian polyomavirus infection in Psittaciformes. In particular, the invention relates to a modified live avian polyomavirus vaccine for preventing avian polyomavirus in Budgerigars, lovebirds and Cockatiels.

2. Background Art

The first acute, generalized infection associated with avian polyomavirus was described in 1980 in young psittacine birds and was called Budgerigar fledgling disease (Davis, R. B., et al., "A viral disease of fledgling budgerigars," *Avian Dis.,* 1981, 25:179–183; Bozeman, L. H., et al., "Characterization of a papovavirus isolated from fledgling budgerigars," *Avian Dis.,* 1981, 25:972–980; Bernier, G., et al., "A generalized inclusion body disease in the budgerigar (*Melopsittacus undulatus*) caused by a papovavirus-like agent," *Avian Dis.,* 1981, 25:1083–1092; Dykstra, M. J., et al., "Investigations of budgerigar fledgling disease virus," *Am. J. Vet. Res.,* 1984, 45:1883–1887; Lehn, H., Muller, H., "Cloning and characterization of budgerigar fledgling disease virus (BFDV), an avian polyomavirus," *Virology,* 1986, 151:362–370). Since its discovery in 1980, avian polyomavirus has been associated with disease in a number of different species of companion and aviary birds including Budgerigars, caiques, macaws, Amazon parrots, conures, cockatoos, lovebirds, Splendid Parakeets, Pionus Parrots, African Grey Parrots, Eclectus Parrots, Cockatiels, finches and lories (Davis et al., 1981; Bozeman et al., 1981; Bernier et al., 1981; Lehn and Muller, 1986; Jacobson, E. R., et al., "Epornitic of papova-like virus-associated disease in a psittacine nursery," *J. Am. Vet. Med. Assoc.,* 1984, 185:1337–1341; Clubb, S. L., Davis, R. B., "Outbreak of papova-like viral infection in a psittacine nursery-a retrospective view," *Proc. Assoc. Avian Vet.*, Toronto, 1984, 121–129; Graham, D. L., "An update on selected pet bird virus infections," *Proc. Assoc. Avian Vet.*, Toronto, 1984, 267–280; Gaskin, J. M., "Psittacine viral disease: A perspective," *J. Zoo. Wildl. Med.,* 1989, 20:249–264; Johnston, K. M., Riddell, C., "Intranuclear inclusion bodies in finches," *Can. Vet. J.,* 1986, 27:432–434; Marshall, R., "Papova-like virus in a finch aviary," *Proc. Assoc. Avian Vet.,* 1989, 203–207; Schmidt, R. E., et al., "Morphologic identification of papovavirus in a Moluccan cockatoo (*Cacatua moluceensis*) with neurologic signs," *Assoc. Avian Vet. Today,* 1987, 1:107–108; Pass, D. A., et al., "A papova-like virus infection of splendid parakeets (*Neophema splendida*)," *Avian Div.,* 1987, 31:680–684; Pass, D. A., "A papova-like virus infection of lovebirds (*Agapornis sp.*)," *Aust. Vet. J.;* 1985, 82:318–319).

The type of clinical disease in Budgerigars, for example, depends upon the age and condition of the bird when exposure to the virus occurs. Neonates from infected flocks may develop normally for 10–15 days and then suddenly die with no premonitory signs. Other infected hatchlings may develop clinical signs that include abdominal distention, subcutaneous hemorrhage, tremors of the head and neck, ataxia and reduced formation of down and contour feathers (Hirai, K., et al., "Isolation of a papova-like agent from young budgerigars with feather abnormalities," *J. Vet Sci.* 46:577–587, 1984; Bernier et al., 1984; Clubb and Davis, 1984; Schmidt et al., 1987; Histopathology Reports #SC90-0637 and #SC90-0638, Schubot Exotic Bird Health Center, Texas A&M University; Vernot, J., personal communication; Dykstra, M. J., Bozeman, L. H., "A light and electron microscopic examination of budgerigar fledgling disease virus in tissue and in cell culture, *Avian Pathol.* 11:11–18, 1982). Infections have also been associated with decreased hatchability and embryonic death (Hudson, L., Hay, F. C., "Isolation and structure of immunoglobulins," Hudson, L., Hay, F. C. Ed., *Practical Immunology*, Boston, 1980, 156–202). Mortality rates can be as high as 100% in affected hatchlings. Surviving birds often exhibit dystrophic primary tail feathers, lack of down feathers on the back and abdomen, and lack of filoplumes on the head and neck. Additionally, surviving birds with primary feather abnormalities are usually unable to fly.

In larger psittacine birds, polyomavirus infections may cause peracute death with no premonitory signs, or acute death after development of clinical changes including depression, anorexia, weight loss, delayed crop-emptying, regurgitation, diarrhea, dehydration, subcutaneous hemorrhages, dyspnea, polyuria, and posterior paresis and paralysis (Pass et al., 1987; Johnston and Riddell, 1986; Mathey, W. J., Cho, B. R., "Tremors of nestling budgerigars with budgerigar fledgling disease," *Proc. 33rd West. Poult. Dis. Conf,* 1984, 102; Woods, L., "Papova-like virus in a purple finch," *J. Zoo. Wildl. Med.,* 1989, 218–219; Gaskin, J. M., "The serodiagnosis of psittacine viral infections," *Assoc. Avian. Vet.*, Honolulu, 1988, 7–10). Characteristic lesions associated with a polyomavirus infection have been demonstrated in companion birds from the United States (Jacobson et al., 1984; Clubb and Davis, 1984; Graham, 1984), Canada (Gough, J. F., "Outbreaks of budgerigar fledgling disease in three aviaries in Ontario," *Can. Vet. J.,* 1989, 30:672–674, Bernier et al., 1984), Japan (Hirai et al., 1984), Italy (Pascucci, S., et al., "Malattia da virus papova-simile nel papagallino ondulato (*Melopsittacus undulatus*), *Clin. Med.* (*Milan*), 1983, 106:38–41), Hungary (Sztojkov, V., et al., " A hullamous papagaj (*Melopsittacus Undulatus*) papovavirus okozta megbetegedesenek hazai megallapitasa, *Magy Allazorv Lapja* 1985, 40:59–63), Germany (Krautwald, M-E, Kaleta, E. F., "Relationship of French moult and early virus induced mortality in nestling budgerigars," *Proc. 8th Intl. Cong. World Vet. Poult. Assoc.,* 1985, 115) and Australia (Pass et al., 1987; Pass, 1985).

Immunodiffusion and virus neutralization techniques have been used to demonstrate anti-polyomavirus antibodies in psittacine birds (Jacobson et al., 1984; Clubb and Davis, 1984; Gaskin, 1989; Davis et al., 1981; Gaskin, 1988; Lynch, J., et al., "Isolation and experimental chicken-embryo-inoculation studies with budgerigar papovavirus," *Avian Dis.* 1984, 28:1135–1139; Wainwright, P. O., et al., "Serological evaluation of some psittaciformes for budgerigar fledgling disease virus," *Avian Dis.* 1987, 31:673–676). During epornitics in mixed psittacine bird collections, infected survivors and asymptomatic birds exposed to them have been shown to develop anti-polyomavirus neutralizing antibodies (Jacobson et al., 1984; Clubb and Davis, 1984; Wainwright et al., 1987). Seronegative young adult birds will seroconvert when housed adjacent to seropositive breeding adults, indicating that an antibody response does occur following natural exposure to the virus (Jacobson et al., 1984; Clubb and Davis, 1984; Wainwright et al., 1987; Davis, R. B., "Budgerigar fledgling disease (FD), *32nd West Poult. Dis. Conf.,* 1983, 104).

Avian polyomavirus infections continue to cause high levels of mortality in companion and aviary birds, resulting in psychological distress for clients and financial burdens for aviculturists and retail distributors despite discovery of the virus over 14 years ago. Therefore, there exists a long-felt need in the art for a safe and effective vaccine against avian polyomavirus which is cross-protective against the disease in multiple species of *Psittaciformes* but especially in Budgregiars, lovebirds and Cockatiels.

SUMMARY OF THE INVENTION

The present invention satisfies the long-felt need in the art for a safe and effective vaccine to protect psittacine birds against avian polyomavirus disease by providing a vaccine which is protective against avian polyomavirus infection in a bird which is classified as being a member of the *Psittaciformes* order, comprising an immunogenic amount of a modified live avian polyomavirus and a pharmaceutically acceptable carrier.

In one embodiment, the vaccine is derived from a strain of avian polyomavirus known as the "L6" strain. In another embodiment, the invention provides a vaccine wherein immunogenic amount of the modified live avian polyomavirus corresponds to a titer of between $10^2$ $TCID_{50}$ and $10^7$ $TCID_{50}$ for the modified live avian polyomavirus, but especially about $10^4$ $TCID_{50}$.

The present invention also provides a method of preventing avian polyomavirus infection in a bird which is classified as being a member of the *Psittaciformes* order, comprising administering to the bird a vaccine comprising an immunogenic amount of a modified live avian polyomavirus and a pharmaceutically acceptable carrier. In one embodiment, the method further comprises administering at least one booster vaccine to the bird.

DETAILED DESCRIPTION OF THE INVENTION

The present invention is more particularly described in the following examples which are intended as illustrative only since numerous modifications and variations therein will be apparent to those skilled in the art.

As used in the claims, "a" can mean one or more, depending on the context of the claim.

The present invention provides a vaccine which is protective against avian polyomavirus infection in a bird which is classified as being a member of the *Psittaciformes* order, comprising an immunogenic amount of a modified live avian polyomavirus and a pharmaceutically acceptable carrier. The term "immunogenic amount" means an amount of an immunogen, i.e., the modified live avian polyomavirus, which is sufficient to induce an immune response in the vaccinated bird and which protects the bird against active infection with wild-type avian polyomavirus upon exposure thereto.

The term "modified live" is intended to refer to a living strain of avian polyomavirus which has been attenuated (modified) by any of a number of methods known in the art including, but not limited to multiple serial passage, temperature sensitive attenuation, mutation, or the like such that the resultant strain is relatively non-pathogenic to a *Psittaciformes* bird. The modified live strain should be capable of infecting the host and inducing a protective immune response which is protective against naturally occurring or wild-type avian polyomavirus.

The birds which can be treated by the invention can be any of the various species of birds which are classified as being members of the *Psittaciformes* order. Examples of such birds include, but are not limited to, Budgerigars (*Melopsittacus undulatus*), caiques (e.g., *Pionites leucogaster leucogaster*), macaws (e.g., *Ara ararauna*), Amazon parrots (e.g., *Amazona ochrocephala auropalliata*, conures (e.g., *Pyrrhara picta, Aratinga wagleri wagleri, Aratinga solstitialis, Aratinga guarouba, Aratinga holochlora rubritorquis* or *Aratinga acuticaudata acuticaudata*), cockatoos (e.g., *Cacatua moluccensis, Cacaiua ducorps, Cacatua sulphura, Cacatua goffini* or *Cacatua alba*), Splendid Parakeets (*Neophema splendida*), Pionus Parrots (*Pionus maximillani*), African Grey Parrots (*Psittacus erithacus erithacus*, Eclectus Parrots (*Electus roratus*), Cockatiels (*Nymphicus hollandicus*) and parakeets (e.g. *Psittacula krameri krameri*). Specifically exemplified by the invention in a preferred embodiment is a vaccine which is protective against avian polyomavirus infection in a bird which is classified as being a member of the *Psittaciformes* order, comprising an immunogenic amount of a modified live polyomavirus and a pharmaceutically acceptable carrier wherein the bird is a Budgerigar, lovebird or a Cockatiel.

It is contemplated that the vaccines of the present invention can be constructed from any isolated strain of avian polyomavirus which infects a member of the *Psittaciformes* order by attenuation utilizing the methods taught herein. For example, the subject avian polyomavirus can be isolated and cultured utilizing the method taught by Bozeman et al., 1981 or by other methods known in the art. Once isolated, the virus can be purified if desired, and serial passaged repeatedly in a cell such as a chicken embryo fibroblast cell, tested for virulence and latency according to methods described herein and the vaccine prepared and the immunogenic dose optimized by the methods taught herein.

In one embodiment of the invention, the avian polyomavirus vaccine is derived from an isolated avian polyomavirus designated the "L6" strain. The L6 strain was adapted from the "L4" strain which was isolated from an infected Budgerigar at the University of Georgia College of Veterinary Medicine in 1981 utilizing the method of Bozeman et al., 1981, and can be obtained from the Laboratory of Dr. Phil D. Lukert, College of Veterinary Medicine, University of Georgia, Athens, Ga. 30602.

One embodiment of the invention provides a vaccine which is protective against avian polyomavirus infection in a bird which is classified as being a member of the *Psittaciformes* order, comprising an immunogenic amount of a modified live avian polyomavirus and a pharmaceutically acceptable carrier, wherein the immunogenic amount of the modified live avian polyomavirus corresponds to a titer of between $10^2$ $TCID_{50}$ and $10^7$ $TCID_{50}$ for the avian polyomavirus.

In a presently preferred embodiment, the immunogenic amount of the modified live avian polyomavirus corresponds to a titer of about $10^4$ $TCID_{50}$ for the avian polyomavirus. As used herein, the immunogenic amount is expressed in terms of "$TCID_{50}$" titer which is given its common meaning in the art of a tissue culture infection dose which infects 50% of the cells of a tissue culture inoculum. Thus, the immunogenic amount of any particular strain of attenuated or modified live avian polyomavirus that is utilized to prepare the vaccines of the invention is based upon the tissue culture infectivity titer for that particular strain of virus. Also, depending upon the species, size and condition of the bird being vaccinated, the immunogenic amount can be varied by the optimization procedures taught herein or by procedures known in the art.

In a presently preferred embodiment, the L6 strain is serial passaged sixteen times and then tested for virulence and latency according to the methods described herein. One of skill in the art can appreciate that the number of serial passages is not critical as long as the passaged strain does not cause the birds to shed a sufficient quantity of viable virus to cause a clinical infection in birds, and it does not induce latent infection, as measured by the methods described herein.

The vaccines of the present invention can be used either alone or in combination with a suitable adjuvant, however, it is generally preferable to utilize the vaccine without an adjuvant.

The vaccine protocol used to administer the immunogenic amount can vary depending upon the species, size and condition of the bird. The vaccine of the invention is typically administered parenterally, either subcutaneously or intramuscularly by injection. It is generally preferable to administer the modified live vaccine to induce infection by an unnatural route such as intramuscular injection.

Of course, the immunogenic amount can be given in divided doses or administered at multiple sites in the bird. Booster immunizations can be given utilizing vaccines containing modified live or whole inactivated avian polyomavirus or any immunogenic portion thereof including recombinant proteins such as VP1 that have been derived from avian polyomavirus.

Modified live strains can be produced by methods which are known in the art including those methods of serial passage in chicken embryo fibroblast cells as set forth in Bozeman, L. H., et al., "Characterization of a papovavirus isolated from fledgling budgerigars," *Avian Dis.,* 1981, 25:972–980. Other cell lines that are known in the art can also be utilized as well as embryonated chicken eggs. Attenuated strains of avian polyomavirus suitable for administration as vaccines can also be obtained by any of the mutagenesis techniques well known to one of ordinary skill in the art. See, *Fundamental Virology,* 2nd Ed., Fields and Knipe, Eds. Raven Press (1990); Sambrook et al., *Molecular Cloning: A Laboratory Manual*, 2nd Ed., Cold Spring Harbor Laboratory, Cold Spring Harbor, New York, (1989) and Ritchie ete al. *Avian Viruses: Function and Control* (1995).

For example, mutations in the nucleotide sequence of a virus can be introduced by chemical mutagenesis, ultraviolet irradiation, serial passage in tissue culture, recombinant DNA protocols, (e.g., insertional or deletion mutagenesis, chimeric construction, synthetic gene construction and the like) or by any other technology designed to introduce alterations in a nucleotide sequence now known or developed in the future. Viruses which have been attenuated can be selected for by techniques well known in the art such as temperature sensitivity, altered growth rate, altered plaque formation, reduced virulence in laboratory animals, antigenic variation, altered immunogenic reactivity, altered reactivity with antiviral drugs or by any other technique designed to select for viruses expressing an altered phenotype due to mutation, either now known or developed in the future.

Attenuated strains of Avian polyomavirus can be tested to determine their immunogenicity by the methods taught in the examples or by other methods known in the art. Briefly, various concentrations of the attenuated strain are prepared and administered to a bird and the immunological response (e.g., the production of antibodies or cell mediated immunity) of the bird to each concentration is determined. The amount of antigen administered will depend upon the species, size and condition of the bird.

Once the antibody response has stabilized, true attenuation of the test strain can be determined by testing for the presence of viremia in the blood of vaccinates utilizing nucleic acid probing, polymerase chain reaction, Elisa testing or other methods known in the art. Gross pathological and microscopic histological examination of tissue specimens from test birds can also be utilized to determine the presence of latent infection. A significant antibody titer without evidence of latent infection is indicative of the appropriate level of attenuation of the vaccine strain.

Thereafter, birds inoculated with the attenuated strain can be exposed to virulent avian polyomavirus to test the potential vaccine effect of the attenuated strain. Once the immunogenicity of attenuated strain is established, the immunogenic amount to be administered to a particular bird can be determined by optimization procedures as taught herein and known in the art.

The vaccines and compositions of the invention can include an effective amount of modified live avian polyomavirus either alone or in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained. It is specifically contemplated that the modified live avian polyomavirus can be administered in a stock cell culture solution. Actual methods of preparing dosage forms are known, or will be apparent, to those skilled in this art; for example, see Martin, E. W., Ed., *Remington's Pharmaceutical Sciences*, latest edition, Mack Publishing Co., Easton, Pa.

Parenteral administration is generally characterized by injection. Injectables can be prepared in conventional forms, either as liquid solutions or suspensions, solid forms suitable for solution or suspension in liquid prior to injection, or as emulsions A more recently revised approach for parenteral administration involves use of a slow release or sustained release system, such that a constant level of dosage is maintained. See, e.g., U.S. Pat. No. 3,710,795.

The present invention also provides a method of preventing avian polyomavirus infection in a bird which is classified as being a member of the *Psittaciformes* order, comprising administering to the bird a vaccine comprising an immunogenic amount of a modified live avian polyomavirus either alone or in combination with a pharmaceutically acceptable carrier. The subject bird of the methods of the invention can be any of the various species of birds which are classified as being members of the *Psittaciformes* order including, but not limited to, the examples cited herein. Specifically provided, however, is a method of preventing avian polyomavirus infection in a bird which is classified as being a member of the *Psittaciformes* order, comprising administering to the bird a vaccine comprising an immunogenic amount of a modified live avian polyomavirus and a pharmaceutically acceptable carrier, wherein the bird is a Budgerigar, a lovebird or a Cockatiel.

In one embodiment, the vaccine utilized in the methods of the invention is derived from an isolated avian polyomavirus designated the L6 strain. However, given the teachings herein it is contemplated that other strains of avian polyomavirus could be utilized as the seed strain for attenuation.

In the methods described herein, the administering step is typically preformed by parenteral administration, i.e., subcutaneous or intramuscular injection of the modified live vaccine into the subject bird. The immunogenic amount of vaccine utilized in the methods of the invention is the same as that provided for in the vaccines of the invention. Specifically, the immunogenic amount of the modified live avian polyomavirus corresponds to a titer of between $10^2$ $TCID_{50}$ and $10^7$ $TCID_{50}$ for the avian polyomavirus but especially about $10^4$ $TCID_{50}$.

The methods of the invention can further comprise the step of administering at least one booster vaccine to the bird. One or more booster inoculations are typically administered at bi-weekly intervals. The first booster vaccine can be administered to the subject bird about two weeks following primary inoculation. If desired, a second booster can be administered in about two weeks.

The booster vaccine can be any of the vaccine preparations contemplated herein but is preferably a repeat immunization with the modified live preparation. In one embodiment, after the initial inoculation, at least one booster vaccine is administered to the bird. The booster vaccine is a composition which produces an anamnestic response against avian polyomavirus infection in a sensitized bird which is classified as being a member of the *Psittaciformes* order. In another embodiment, the booster can comprise an anamnestic response inducing amount of a recombinant protein of avian polyomavirus and a pharmaceutically acceptable carrier. The booster vaccine can be comprised of any recombinant protein derived from avian polyomavirus or an immunogenic polypeptide fragment thereof In one embodiment, the recombinant protein is the VP1 capsid protein.

A recombinant protein such as the VP1 protein produces a specific antibody response in the animal to only a portion of the virus. Secondary response to a specific immunogenic protein greatly reduces the risks associated with booster vaccination. Reaction to the booster can be milder yet sufficiently immunogenic to boost the bird's primary immunity to the virus.

Throughout this application, various publications are referenced. The disclosures of these publications in their entireties are hereby incorporated by reference into this application in order to more fully describe the state of the art to which this invention pertains.

EXAMPLES

Example 1: Modified Live Avian Polyomavirus Vaccine-Trial 1

Material and Methods

Virus: A stock strain of "L6" avian polyomavirus (passage level 11), recovered originally from infected Budgerigars (*Melopsittacus undulatus*), was grown in chicken embryo fibroblasts in M199 with 5% calf serum and was used for the experiments described in this study. Flasks of infected cells were grown for 7 days and were then frozen and thawed one time and suspended in a cell culture solution containing gentamicin and amphotesicin B. The virus-containing supernatant (50 ml) was serially diluted in a MICROTITER plate containing a 24-hour monolayer of primary chicken embryo fibroblasts. This preparation had an infectivity titer about of $10^4$ $TCID_{50}$ per ml. Virus neutralizing antibody assay: Polyomavirus neutralizing antibody titers were determined according to published procedures (Lukert, P. D., "Budgerigar fledgling disease," Purchase H. G., et al., Ed., *A Laboratory Manual for the Isolation and Identification of Avian Pathogens*, Kennet Square: Am. Assoc. Avian Pathol., 1989:106–107) with the exception that the chicken embryo fibroblasts were fixed with 95% ethanol and stained with crystal violet to detect CPE. Antibody titers were expressed as the reciprocal of the serum dilution that protected the chicken embryo fibroblasts from detectable cytopathic effects.

Vaccine preparation: The purified virus used to produce the vaccine in this study had a titer of about $10^4$ $TCID_{50}$ of cell culture solution.

Vaccination protocol: A group of 5 mature budgerigars that were shown to be negative for avian polyomavirus neutralizing antibodies was used in our initial vaccine trial. Two of these birds were inoculated by the combined intraoral, intranasal and intraocular routes with a suspension of master seed virus containing approximately $10^4$ $CID_{50}$ ml. Three birds were injected with the same suspension intramuscularly. Serum was collected from each bird on days 0, 10 and 20. The virus neutralizing antibody titers detected in each bird are listed in table 1.

DNA probe detection of polvomavirus nucleic acid to determine latency: Whole blood samples from these vaccinated birds can be collected at regular biweekly intervals in sodium heparin (20 μl heparin per ml of blood) for approximately 30-days post vaccination or until no viremia is detected. Samples can be processed for detection of viremia, i.e., polyomavirus nucleic acid, using amplification procedures and viral-specific DNA probes according to a modification of published procedures (Niagro, F. D., et al., "Use of polymerase chain reaction for detection of BFD in suspect birds," *Proc. Assoc. Avian Vet.,* Phoenix, 1990, 25–37). Cloacal swabs can also be collected from the chicks to probe for the presence of viral nucleic acids. The swabs should be collected before feeding each morning. These swabs can be processed for detection of polyomavirus nucleic acid, as described previously (Davis et al., 1981).

Additionally, latent infection with the attenuated virus and the need for further attenuation can be ascertained following the cessation of viremia by euthanizing vaccinated birds and collection of tissues (liver, spleen, kidney and bone marrow) for in situ hybridization and nucleic acid amplification using viral specific DNA probes. The inability to detect viral nucleic acid in the tissues that are considered the usual site for viral persistence will prove the suitability the test strain of our modified-live vaccine for field use.

Results: None of the chicks used in this study had detectable levels of polyomavirus neutralizing (VN) antibodies at the beginning of the study. The results of the virus-neutralizing essay indicated that the modified-live virus replicated in the birds that were injected intramuscularly (considered an unnatural route of exposure) but not in the birds inoculated by the combined intraoral, intranasal and intraocular routes (considered a natural route of exposure).

Table 1 (below) clearly shows VN antibody titers in birds 3, 4, and 5 at Day 20 which correlate with protective immunity for *Psittaciformes* birds.

Table 1: Virus-neutralizing antibody titers following injection with modified-live avian polyomavirus. Birds 1 and 2 were inoculated by the combined intraoral, intranasal and intraocular routes. Birds 3, 4 and 5 were inoculated intramuscularly.

TABLE 1

| Bird | Day 0 | Day 10 | Day 20 |
|---|---|---|---|
| 1 | 0 | 0 | 0 |
| 2 | 0 | 0 | 0 |
| 3 | 0 | 40 | 40 |
| 4 | 0 | 10 | 80 |
| 5 | 0 | 20 | 160 |

Example 2: Modified Live Avian Polyomavirus Vaccine—Trial 2

Vaccination protocol: Five mature budgerigars, previously shown to be negative for avian polyomavirus neutralizing antibodies, were used in this trial. Four birds were inoculated intramuscularly with approximately $10^4$ $TCID_{50}$/ml of a modified live viral vaccine strain (passage 5 from L6). The fifth bird served as a contact control to indicate whether inoculated birds were shedding virus that would infect the control.

TABLE 2

Virus Neutralizing (VN) Antibody Titers in Birds Vaccinated with Modified Live Avian Polyomavirus (MLV)

| Bird/ Treatment | Day 0 | 1 month | 2 months | 4 months | 12 montbs |
|---|---|---|---|---|---|
| 1. control | 0 | 0 | 0 | 0 | 0 |
| 2. inoculated | 0 | 20 | 20 | 20 | 10 |
| 3. inoculated[a] | 0 | 20 | 40 | 80 | 80 |
| 4. inoculated | 0 | 40 | 20 | 40 | 40 |
| 5. inoculated | 0 | 80 | 160 | 320 | 80 |

[a]This bird was necropsied and tissues evaluated.

Results: The data presented in Table 2. indicates 1) that the modified live viral vaccine strain replicates in birds that are injected intramuscularly, and 2) that none of these birds shed a sufficient quantity of viable virus to cause an infection in unvaccinated birds through contact, which is a common means of viral spread. The necropsy and histological evaluation of the indicated bird showed no microscopic changes that would suggest an active polyomavirus infection, and in situ hybridization of the liver, spleen and kidney, according to the protocol described above, were negative for polyomavirus nucleic acid. The negative results from in sutu hybridization indicate that this vaccine strain does not induce latent infections.

Although the present process has been described with reference to specific details of certain embodiments thereof, it is not intended that such details should be regarded as limitations upon the scope of the invention except as and to the extent that they are included in the accompanying claims.

What is claimed is:

1. A vaccine which is protective against avian polyomavirus infection in a bird which is classified as being a member of the *Psittaciformes* order, comprising an immunogenic amount of a modified live avian polyomavirus, wherein the immunogenic amount of the modified live avian polyomavirus corresponds to a titer of between $10^2$ $TCID_{50}$ and $10^7$ $TCID_{50}$ and a pharmaceutically acceptable carrier.

2. The vaccine of claim 1, wherein the immunogenic amount of the modified live avian polyomavirus corresponds to a titer of about $10^4$ $TCID_{50}$ for the avian polyomavirus.

3. The vaccine of claim 1, wherein the bird is a Budgerigar.

4. The vaccine of claim 1, wherein the bird is a Cockatiel.

5. The vaccine of claim 1, wherein the bird is a lovebird.

6. A method of preventing avian polyomavirus infection in a bird which is classified as being a member of the *Psittaciformes* order, comprising administering to the bird a vaccine comprising an immunogenic amount of a modified live avian polyomavirus and a pharmaceutically acceptable carrier.

7. The method of claim 6, wherein the immunogenic amount of the modified live avian polyomavirus corresponds to a titer of between $10^2$ $TCID_{50}$ and $10^7$ $TCID_{50}$ for the avian polyomavirus.

8. The method of claim 7, wherein the immunogenic amount of the modified live avian polyomavirus corresponds to a titer of about $10^4$ $TCID_{50}$ for the avian polyomavirus before inactivation.

9. The method of claim 6, wherein the bird is a Budgerigar.

10. The method of claim 6, wherein the bird is a Cockatiel.

11. The method of claim 6, wherein the bird is a lovebird.

12. The method of claim 6, further comprising administering at least one booster vaccine to the bird.

* * * * *